United States Patent
Siccardi et al.

(10) Patent No.: US 12,419,652 B2
(45) Date of Patent: Sep. 23, 2025

(54) BROACH HANDLE FOR A RASP AND SURGICAL DEVICE COMPRISING SAID HANDLE

(71) Applicant: MEDACTA INTERNATIONAL SA, Castel San Pietro (CH)

(72) Inventors: Francesco Siccardi, Castel San Pietro (CH); Frederic Laude, Castel San Pietro (CH); Massimiliano Bernardoni, Castel San Pietro (CH); Christian Trombetta, Castel San Pietro (CH); Ermete Rossi, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 460 days.

(21) Appl. No.: 17/772,080

(22) PCT Filed: Nov. 3, 2020

(86) PCT No.: PCT/IB2020/060286
§ 371 (c)(1),
(2) Date: Apr. 26, 2022

(87) PCT Pub. No.: WO2021/090151
PCT Pub. Date: May 14, 2021

(65) Prior Publication Data
US 2022/0401113 A1    Dec. 22, 2022

(30) Foreign Application Priority Data
Nov. 7, 2019    (IT) .......................... 102019000020576

(51) Int. Cl.
*A61B 17/16* (2006.01)
*A61B 17/00* (2006.01)

(52) U.S. Cl.
CPC ........ *A61B 17/1659* (2013.01); *A61B 17/164* (2013.01); *A61B 17/1668* (2013.01);
(Continued)

(58) Field of Classification Search
CPC .............. A61B 17/1659; A61B 17/164; A61B 17/1668; A61B 2017/0046; A61B 2017/00738
(Continued)

(56) References Cited

U.S. PATENT DOCUMENTS

| | | | |
|---|---|---|---|
| 4,583,270 A | 4/1986 | Kenna | |
| 4,671,275 A | 6/1987 | Deyerle | |

(Continued)

FOREIGN PATENT DOCUMENTS

| | | | |
|---|---|---|---|
| AU | 2011244995 A1 | 12/2011 | |
| JP | S59200641 A | 11/1984 | |

(Continued)

OTHER PUBLICATIONS

Notice of Reasons of Refusal with English Translation in JP 2022-526131, mailed May 24, 2023, 20 pages.
(Continued)

*Primary Examiner* — Jessica Weiss
(74) *Attorney, Agent, or Firm* — Meunier Carlin & Curfman LLC

(57) ABSTRACT

A broach handle for a rasp includes a proximal part extending along a first axis between a first portion of the handle and a second portion of the handle, and a proximal part extending partially along a second axis between a third portion of the handle, connected to the second portion, and a fourth portion of the handle, and partially along a third axis between a fifth portion of the handle, connected to the fourth portion, and a sixth portion of the handle connectable to a rasp. The sixth portion of the handle has a connection
(Continued)

surface for connecting to the rasp having a normal extending along a normal axis defining a connection axis between the handle and the rasp. A first convex angle is defined between the first axis and the second axis, and a second convex angle is defined between the third axis and the normal axis.

23 Claims, 6 Drawing Sheets

(52) U.S. Cl.
  CPC ................. *A61B 2017/0046* (2013.01); *A61B 2017/00738* (2013.01)

(58) Field of Classification Search
  USPC .......................................................... 606/85
  See application file for complete search history.

(56) References Cited

U.S. PATENT DOCUMENTS

| | | | | |
|---|---|---|---|---|
| 8,657,833 | B2* | 2/2014 | Burgi | A61F 2/4607 606/99 |
| 11,596,420 | B2* | 3/2023 | Tsukayama | A61B 17/155 |
| 11,602,359 | B2* | 3/2023 | Clements | A61B 17/1659 |
| 2003/0220698 | A1 | 11/2003 | Mears et al. | |
| 2010/0121331 | A1 | 5/2010 | Sharp et al. | |
| 2014/0121650 | A1 | 5/2014 | Thomsen et al. | |
| 2017/0367714 | A1* | 12/2017 | McCulloch | A61F 2/4607 |
| 2018/0028196 | A1* | 2/2018 | Sharkey | A61F 2/4637 |
| 2022/0401113 | A1* | 12/2022 | Siccardi | A61B 17/164 |

FOREIGN PATENT DOCUMENTS

| | | |
|---|---|---|
| JP | 2004358215 A | 12/2004 |
| JP | 2013511351 A | 4/2013 |
| WO | 2011063173 A2 | 5/2011 |

OTHER PUBLICATIONS

International Search Report and Written Opinion issued in PCT/IB2020/060286, mailed Jan. 18, 2021.

* cited by examiner

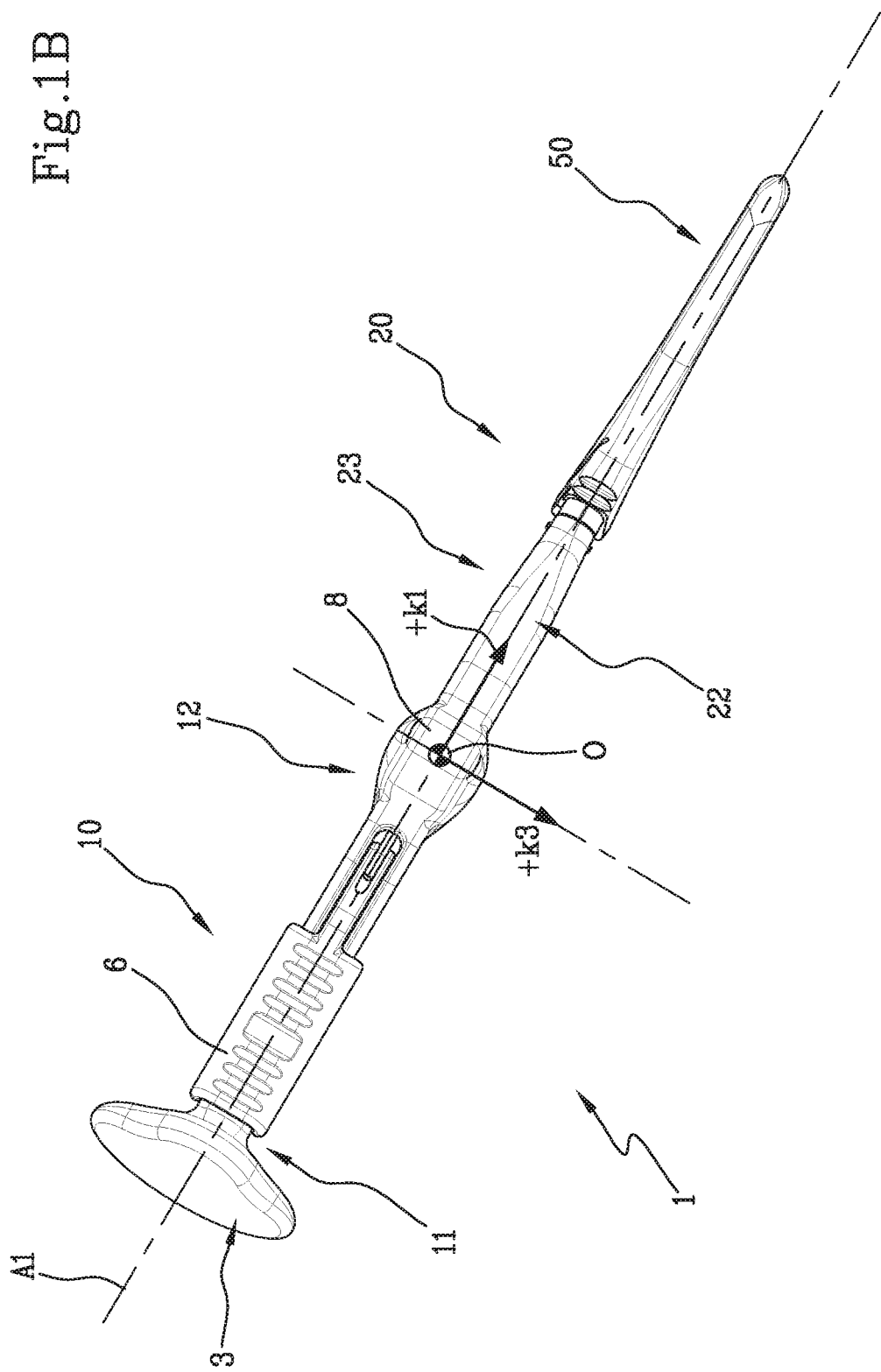

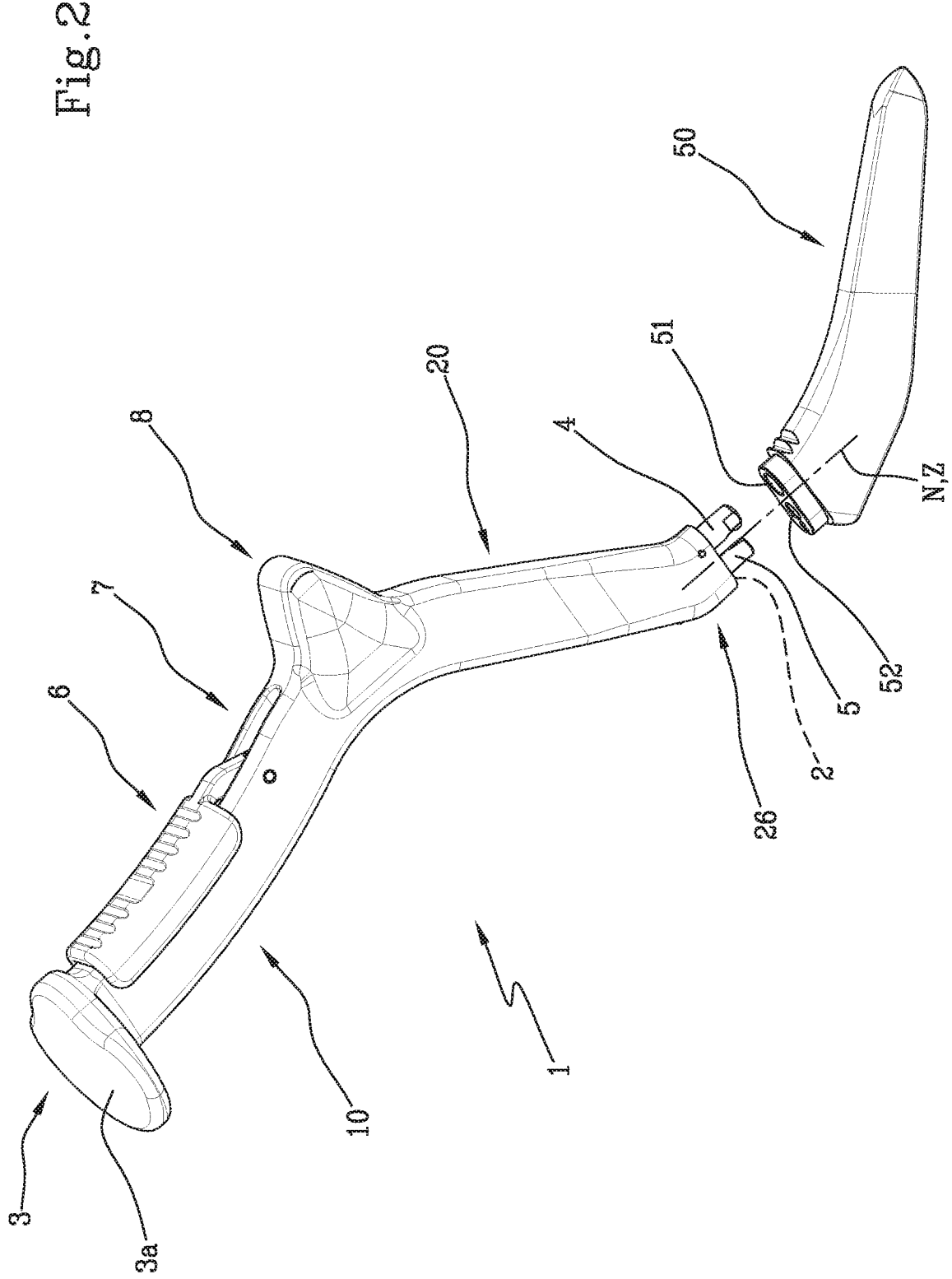

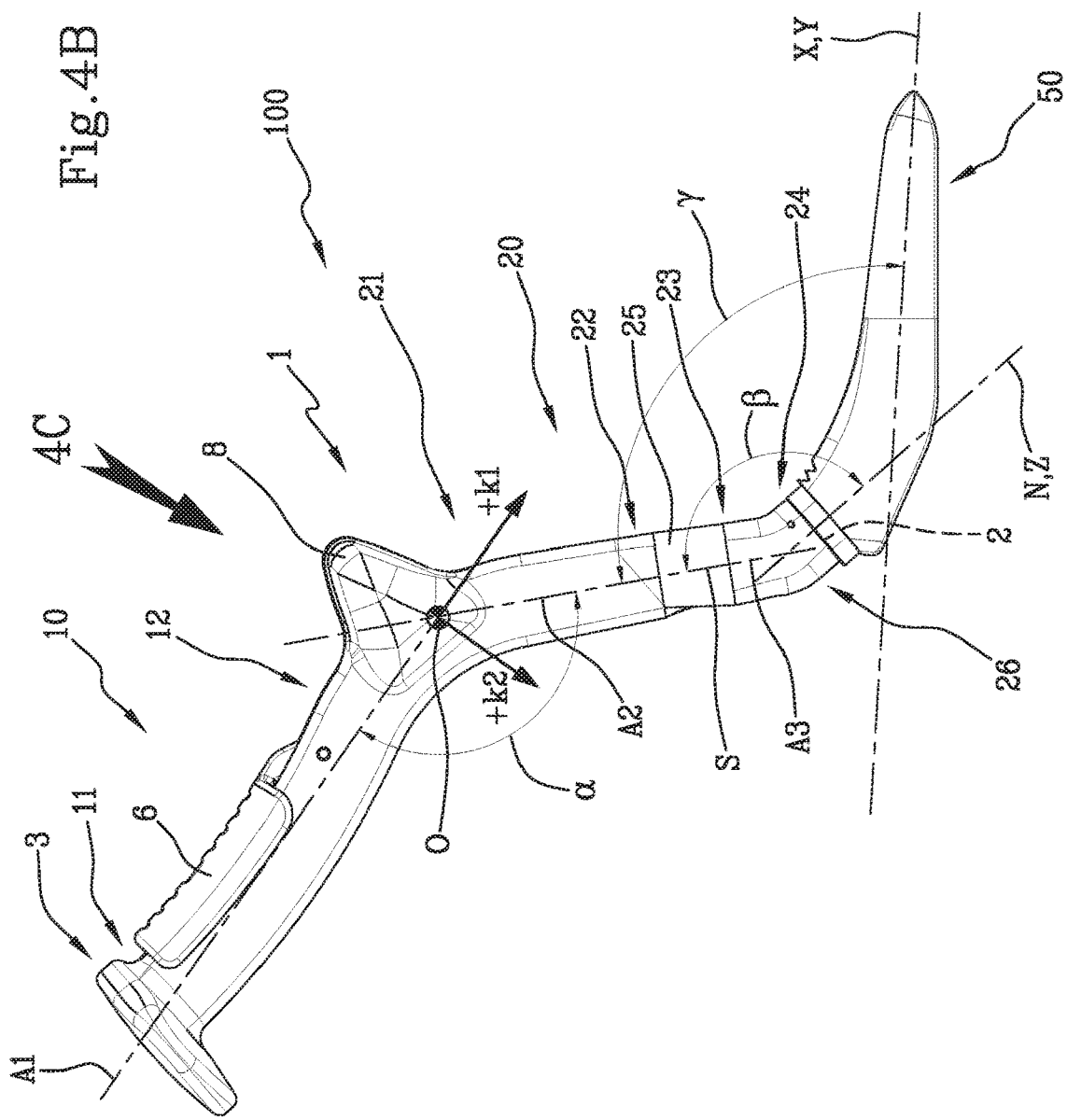
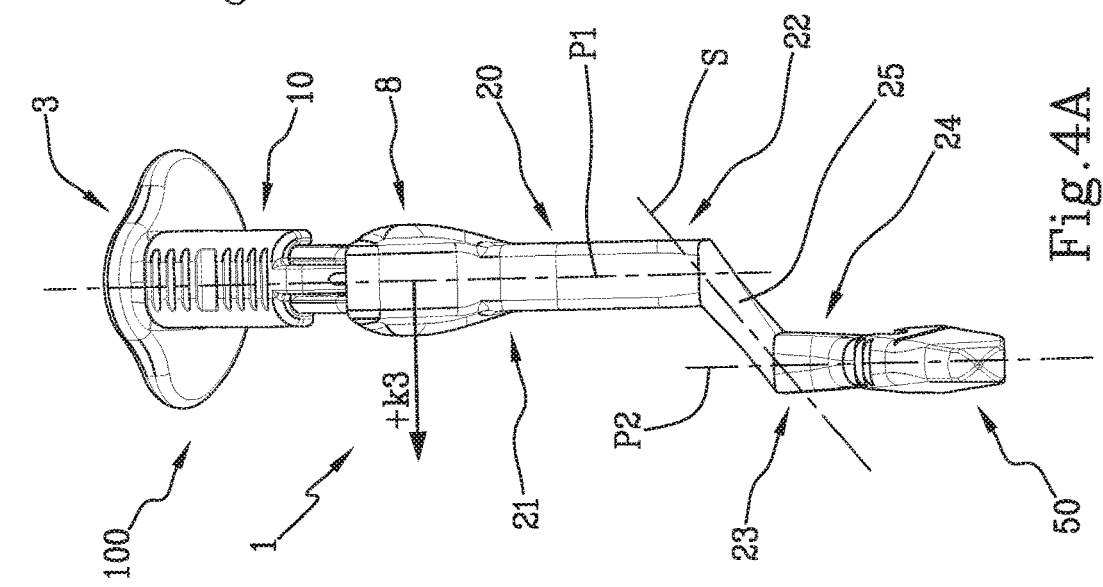

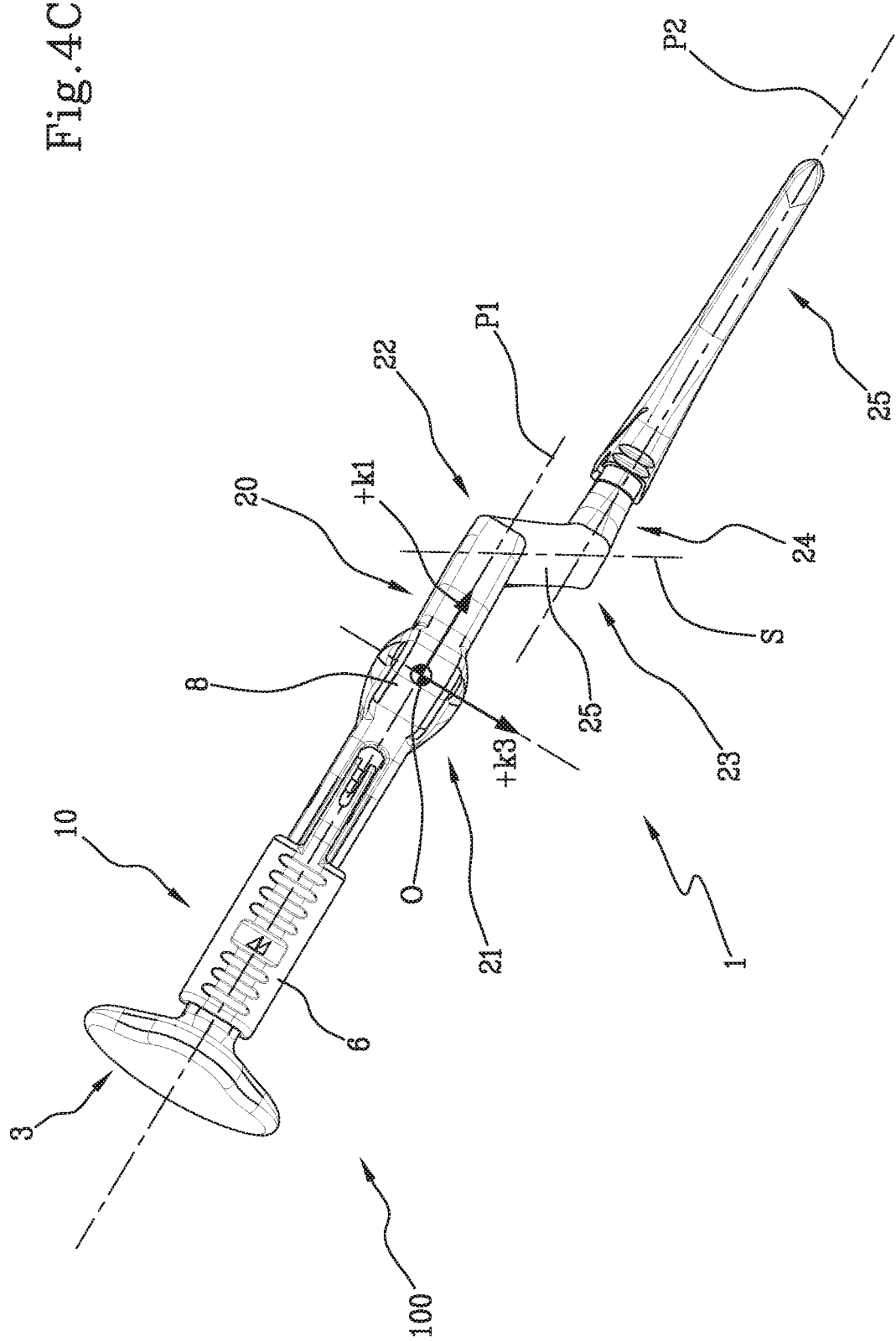

BROACH HANDLE FOR A RASP AND SURGICAL DEVICE COMPRISING SAID HANDLE

The present application is a national stage of International Application No. PCT/IB2020/060286, filed on Nov. 3, 2020, which claims the priority from Italian Patent Application No. 102019000020576, filed on Nov. 7, 2019, both of which are hereby incorporated by reference in their entireties.

FIELD OF THE INVENTION

This invention relates to a rasp handle and a surgical device for the preparation of a femoral canal comprising said handle.

The invention finds application in the field of orthopaedic surgery, particularly in arthroplasty or hip joint replacement, where the damaged bone portion and cartilage are removed and replaced with artificial prosthetic components.

Hip prostheses replace the natural joints that are no longer functioning and affect both the femur and the acetabulum.

PRIOR ART

When the damaged joint has to be operated on, the upper part of the femur, consisting of the head and neck, is usually removed; the acetabulum portion within which the femur is housed is covered with an acetabular cup; and, subsequently, the so-called prosthetic stem is applied inside the femoral canal.

The damaged femoral head is removed and replaced with a prosthetic device comprising a stem, e.g. a metal stem, inserted into the medullary canal of the femur and a joint unit comprising the femoral head. One end of the stem is in fact specially made to fit inside the femoral medullary canal specially prepared by the surgeon, while the other end has a head, very similar to the native one of the femur, suitable for being placed inside the prosthetic acetabular cup.

To prepare the femoral canal to receive the prosthetic stem inside it, after the initial excision of the femoral head, the surgeon proceeds with a step for rasping the severed femoral section.

Typically, an instrument with a rasp is used for rasping, also called "sickle knife rasp" or more simply "rasp", having a shape similar to a sickle or a rhinoceros horn, connected to a surgical device gripping handle that is repeatedly beaten with a hammer to progressively insert the rasp into the femoral canal, exerting a rasping action.

Starting from the smallest rasp, the surgeon proceeds with the preparation of the femoral canal, slowly increasing the size of the rasp until it corresponds to the size of the stem to be inserted.

This technique represents to date one of the least invasive techniques for total hip arthroplasty.

However, the Applicant has noted some drawbacks that occur during the operating steps.

With the patient lying supine, after having placed the leg to be operated in hyperextension and severed the femoral head, in order to correctly rasp the femur and prepare the femoral canal, the surgeon must rotate the femur to expose both the severed femoral head and, at least partially, the femur from its natural seat in order to correctly insert the rasp into the medullary canal of the femur.

This operation, besides being very delicate and requiring the surgeon's special care subjects the femur to potential trauma and external contamination, and requires an extensive incision in the patient's epidermis.

However, partial exposure of the femur is necessary so that the surgeon has a good view of the operating site and can insert the rasp connected to the surgical device handle into the medullary canal of the femur.

The handles of the surgical devices used today are basically straight and the angle formed between the extension axis of the handle and the extension axis of the rasp connected to it is approximately equal to a flat angle. This conformation therefore defines a substantially straight surgical device that is only partly maneuverable during all the operating steps and uncomfortable during the insertion of the rasp into the femur: for this reason, it is essential to expose at least part of the femoral canal that the device cannot otherwise reach.

The surgical steps that must be performed for total hip arthroplasty, with the use of currently known devices, involve cutting the head of the femur followed by a step for hyperextending the leg and subsequently rotating the same. Subsequently, the step known in jargon as "femoral release" is implemented, which involves the femur coming out of its natural seat: this manoeuvre involves moving the upper part of the femur towards the wound. At this point, the surgeon can proceed with the rasping of the femoral canal by inserting the rasp inside the femoral canal using the known handle.

The femoral release step is particularly stressful for the physical structure of the patient and also implies a longer surgical operating time. In addition, this manoeuvre may result in more pain for the patient and, therefore, longer recovery times.

The "femoral release" step is indispensable with currently known surgical devices since, if the femur is not removed from its natural seat, the body of the handle of the surgical device carrying the rasp would interfere with the pelvic bone. With the femoral release, on the other hand, the interaction/impingement with the patient's soft tissue is avoided.

The inclination with respect to the femoral axis of the surgical device currently used interferes with the patient's pelvis and abdomen, so the femur must be at least partially exposed to the outside in order to receive the device rasp.

The conformation of the known devices is also problematic in the case of operations on patients with an excessive abdominal fat layer: in these cases, in fact, the interaction between the device itself and the patient's skin is highly probable, with possible consequent trauma to the patient's skin.

In this context, the technical task underlying this invention is to propose a broach handle for the rasp and a surgical device comprising said handle that overcome one or more of the above-mentioned drawbacks of the prior art.

In particular, it is the purpose of this invention to provide a handle with an optimised geometry for connecting to a rasp, improving the efficiency and effectiveness of the operating steps for the preparation of a femoral canal.

An additional purpose of this invention is to propose a surgical device for the preparation of a femoral canal that is comfortable for the surgeon to use and that enables the rasp to be inserted into the femur quickly and easily.

Finally, the purpose of this invention is to propose a surgical device for the preparation of the femoral canal that reduces operating times and avoids operating steps that are particularly traumatic for the bone structure or stressful for the patient's own soft tissue.

The specified technical task and purposes are basically achieved with a broach handle for a rasp and a surgical device for the preparation of a femoral canal comprising the technical features set forth in one or more of the accompanying claims.

SUMMARY

In a first aspect, this invention provides a broach handle for a rasp comprising:
a proximal part extending along a first axis between a first portion of the handle and a second portion of the handle, and
a distal part extending partially along a second axis between a third portion of the handle, connected to the second portion, and a fourth portion of the handle, and extending partially along a third axis between a fifth portion of the handle, connected to the fourth portion, and a sixth portion of the handle connectable to a rasp.

In particular, the first axis, the second axis, the third axis, and the normal axis lie on the same placement plane.

Alternatively, the proximal part comprises a skew portion extending, between the fourth portion and the fifth portion of the handle, along a skew axis that is transverse in relation to the second axis and the third axis.

Advantageously, the sixth portion of the handle has a connection surface for connecting to the rasp with a normal extending along a normal axis defining a connection axis between the handle and the rasp, wherein a first convex angle is defined between the first axis and the second axis and a second convex angle is defined between the third axis and the normal axis.

The handle, according to this invention, therefore has a double convexity so that, by suitably sizing the value of the first and second convex angle, it is possible to provide the surgeon with a handle optimized for the morphological and physiological characteristics of the patient, which makes the rasp insertion operation and the rasping itself more efficient.

According to another aspect of this invention, there is also a surgical device for the preparation of a femoral canal comprising a handle in accordance with this invention and a rasp extending along a prevailing extension axis coinciding with an insertion axis of the rasp inside a femur for the preparation of a femoral canal. In particular, the rasp is connected to the handle at the connection surface of the handle along the connection axis for connecting to the rasp so that between the prevailing extension axis of the rasp and the third axis of the handle a convex inclination angle of the rasp is defined.

Thanks to the double convexity, the surgical device therefore has a geometry that enables it to avoid interfering with the patient's abdomen and pelvis when in use.

In particular, by using the device according to this invention, it is possible to rasp the medullary canal of the femur without having to extract the femur from its natural seat, which can in fact be reached comfortably by the rasp, since it is inclined with respect to the distal portion of the handle, thus limiting the size of the incision necessary for insertion into the femur.

The invention therefore makes it possible to speed up hip surgery by limiting the risk of joint injuries and ensuring the highest possible level of sterility.

According to another aspect of this invention, a surgical device for the preparation of a femoral canal is provided, comprising a broach handle and a rasp irreversibly connected to each other, i.e. made of one piece.

The rasp extends along a prevailing extension axis coinciding with an insertion axis of the rasp into a femur for the preparation of a femoral canal.

The handle comprises a proximal part and a distal part.

The proximal part extends along a first axis between a first portion of the handle and a second portion of the handle, while the distal part extends partially along a second axis between a third portion of the handle, connected to the second portion, and a fourth portion of the handle, and partially along a third axis between a fifth portion of the handle, connected to the fourth portion, and a sixth portion of the handle connected to the rasp.

Advantageously, a first convex angle is defined between the first axis and the second axis, and a convex inclination angle of the rasp is defined between the prevailing extension axis of the rasp and the third axis of the handle.

The first axis, the second axis, the third axis, and the prevailing extension axis of the rasp lie on the same placement plane. Alternatively, the distal part of the handle comprises a skew portion extending, between the fourth portion and the fifth portion of the handle, along a skew axis transverse in relation to the second axis and the third axis.

The dependent claims, included herein for reference, correspond to different embodiments of the invention.

BRIEF DESCRIPTION OF THE DRAWINGS

Additional characteristics and advantages of this invention will become more apparent from the indicative, and therefore non-limiting, description of one preferred, but not exclusive, embodiment of a broach handle for a rasp and a surgical device for the preparation of a femoral canal comprising said handle, as illustrated in the attached figures, wherein:

FIG. 2 is an exploded schematic perspective view of the device shown in FIG. 1A;

FIGS. 4A and 4B are, respectively, a front schematic view and a side schematic view of a second embodiment of a handle for a rasp and of a surgical device for the preparation of a femoral canal in accordance with this invention; and FIGS. 1B and 4C are comparative schematic side views of the handle and the device in FIGS. 1A and 4B respectively.

DETAILED DESCRIPTION OF PREFERRED EMBODIMENTS OF THE INVENTION

Figure 1A:
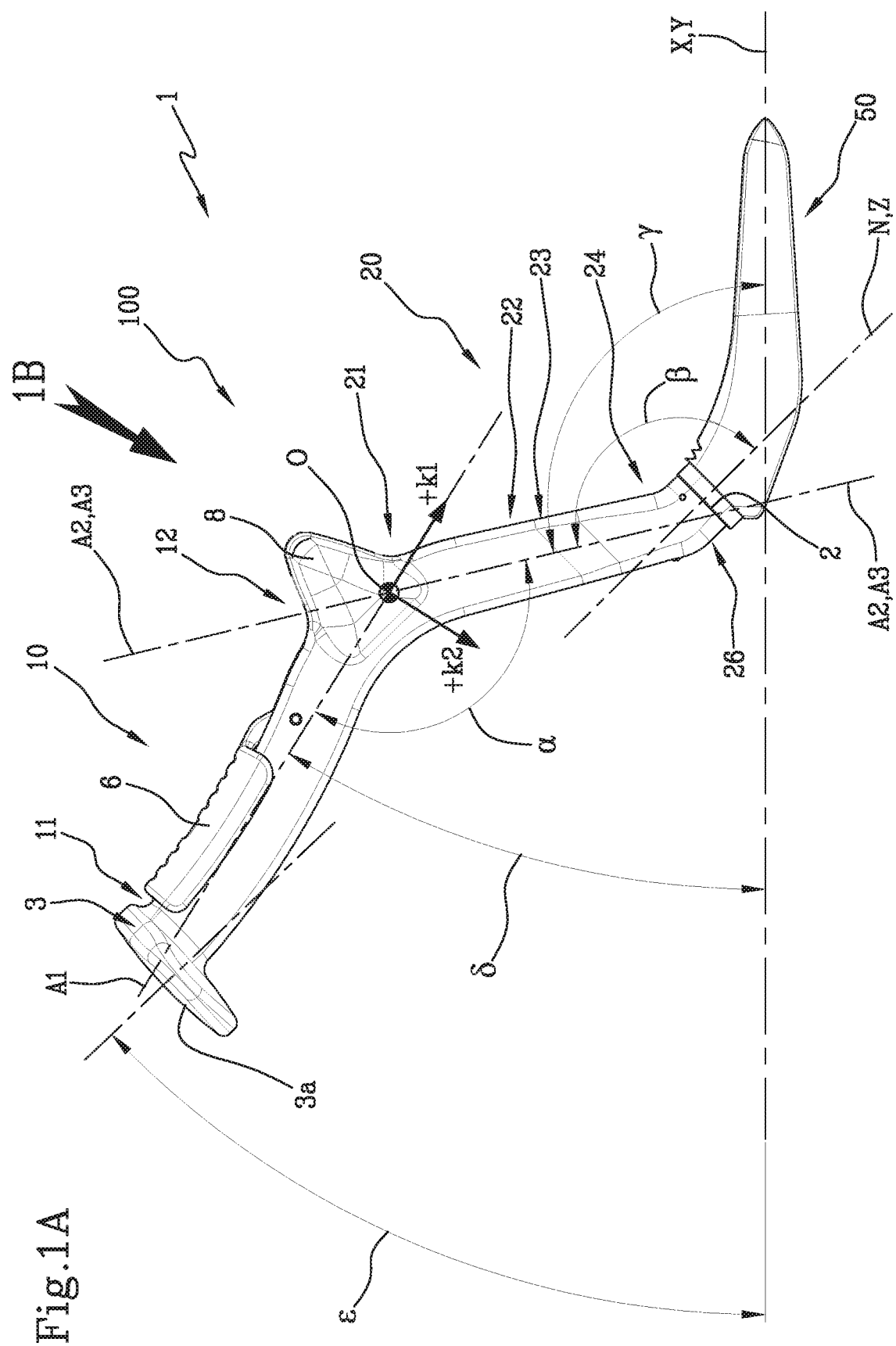
FIG. 1A is a schematic side view of a first embodiment of a handle for a rasp and of a surgical device for the preparation of a femoral canal according to this invention.

With reference to the attached figures, the reference number 100 indicates, as a whole, a surgical device for the preparation of a femoral canal, from hereon in, simply, the device 100.

The device 100 comprises a broach handle for a rasp 1, from hereon in, simply, the handle 1, and a rasp 50 connected to the handle 1.

Figure 3:
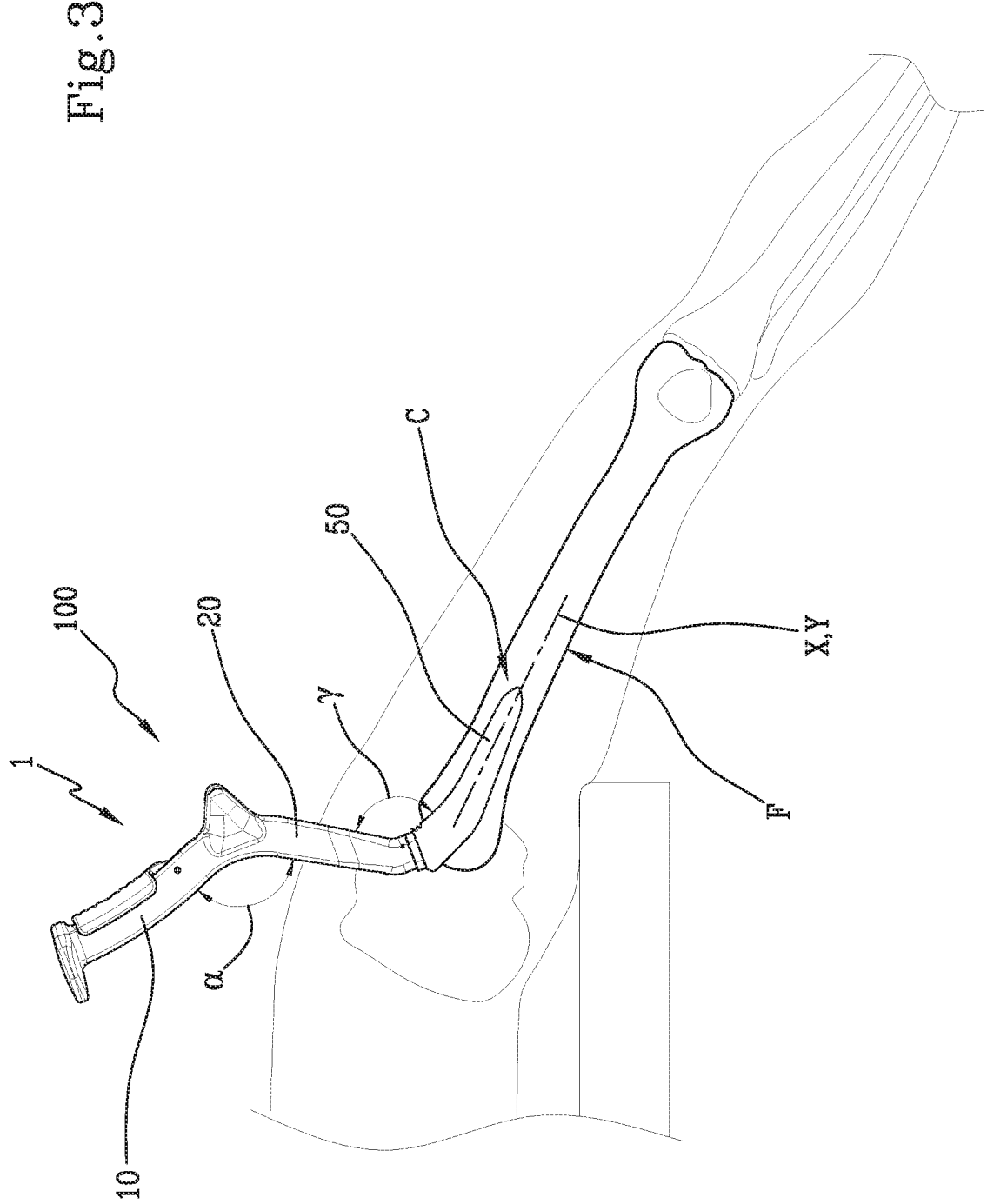
FIG. 3 is a schematic side view of the device in FIG. 1A during an operating step wherein the rasp is inserted into a patient's femur.

With reference to FIG. 3, the rasp 50 is designed to be inserted along a insertion axis Y, inside the medullary canal of the femur F of a patient, to prepare a femoral canal C inside of which it is possible to install a prosthetic stem, which is not illustrated.

After the step of cutting the head of the femur, in particular, the operating procedure involves the hyperextension of the leg, the femur F of the patient being preventatively extra-rotated towards the outside of the body so as to sufficiently expose the severed femoral head to the surgeon for the insertion of the rasp 50. In the example illustrated in FIG. 3, the femur is rotated approximately 90° around its own axis in relation to its natural position.

The rasp 50 illustrated in the attached figures extends along a prevailing extension axis X coinciding with an insertion axis Y of the rasp inside the femur F.

The rasp 50 preferably comprises a multitude of superficial crests, not illustrated, configured to exert a rasping action during the repeated insertion of the rasp 50 inside the medullary canal of the femur F.

The rasp 50, illustrated in the attached figures, preferably has a basically truncated pyramid shape, wherein the directrix follows a curved or fragmented trajectory coinciding, for a predominant section, with the prevailing extension axis X, defining a "sickle" shape. In other words, the directrix of the truncated pyramid deviates at the connection zone with the handle 1.

The handle 1, to which this invention relates, comprises a proximal part 10 and a distal part 20.

In particular, the term "proximal" is intended to refer to the part of the handle 1 closest to the surgeon while the term "distal" the part furthest from the body of the surgeon.

With reference to the attached figures, therefore, the term "proximal part" 10 is intended to refer to the part of the handle 1 that, in use, is arranged furthest from the body of the patient, while the term "distal part" 20 is intended to refer to the part of the handle 1 that, in use, is arranged closest to the patient's body. In particular, the proximal part 10 defines the part of the handle 1 that the surgeon grasps, while the distal part 20 is the part of the handle 1 connected or connectable to the rasp 50.

With particular reference to FIGS. 1A and 4B, the proximal part 10 extends along a first axis A1 between a first portion 11 of the handle 1 and a second portion 12 of the handle 1.

The distal part 20 extends:
partially along a second axis A2 between a third portion 21 of the handle 1, connected to the second portion 12, and a fourth portion 22 of the handle 1, and
partially along a third axis A3 between a fifth portion 23 of the handle 1, connected to the fourth portion 22, and a sixth portion 24 of the handle 1 connectable to a rasp 50.

It should be noted that the term "axis" A1, A2, A3 is intended to refer to a prevailing extension direction.

The sixth portion 24 has, in particular, a connection surface 2 for connecting to the rasp 50, preferably a planar surface, with a normal extending along a normal axis N defining a connection axis Z connecting the handle 1 with the rasp 50.

The connection surface 2 preferably defines the free end of the sixth portion 24.

Advantageously, a first convex angle α is defined between the first axis A1 and the second axis A2, and a second convex angle β is defined between the third axis A3 and the normal axis N, so that the handle 1 according to this invention, if seen from the side, as show in FIGS. 1A and 4B, does not have a straight extension, i.e. it is not aligned in a single, prevailing extension axis.

In particular, the first convex angle α defines the inclination value between the proximal part 10 and the distal part 20, while the second angle β defines the inclination between the connection axis Z connecting the handle 1 with the rasp 50 and the axis A3.

As illustrated in the attached figures, the term "first angle α" refers, thus, to the convex angle arranged between the proximal portion 10 and the distal portion 20, while the term "second angle β" refers to the convex angle opposite the first angle α in relation to the distal portion 20 of the handle 1. In other words, the two angles α, β are opposite each other in relation to the volume of the handle 1.

With reference to FIGS. 1A and 4B, the first angle α preferably has a value ranging between 90° and 180°, even more preferably being equal to 135°.

With reference to FIGS. 1A and 4B, the second angle β preferably has a value ranging between 125° and 165°, even more preferably being equal to 150°.

The presence of two convexities, defined by the angels α and β, make it possible, advantageously, to create a handle 1 conveniently designed so as not to interfere with the abdomen of the patient and that, at the same time, makes it possible to insert the rasp 50 inside the severed head of the femur F without having to extract it from its seat.

In FIGS. 1A, 1B, 4A, 4B, and 4C, k1, k2, k3 indicate a Cartesian reference system with the "O" origin at the intersection of the A1 and A2 axes, i.e. at the ideal separation point between the proximal part 10 and the distal part 20 of the handle 1. In particular, with reference to FIGS. 1A and 4B, the Cartesian term k1, k2, k3 is oriented so that k1 coincides with the axis A1 and so that k3 is perpendicular to the sheet.

In this regard, it should be noted that FIGS. 1B and 4C are side views oriented so that k2 is oriented with a direction outside the sheet.

In accordance with this reference system, the proximal part 10 thus extends mainly along the direction k1, oriented in the negative direction, thus direction −k1.

The first angle α and the second angle β preferably have respective convexities turned in opposite directions in relation to the handle itself, or, in particular, in relation to the distal portion 20 of the handle.

Advantageously, opposite convexities make it possible to create a handle 1 in which the distal part 20 extends away from the body of the patient, reducing the dimensions in the abdominal zone, and in which the proximal part 10 has an inclination in relation to the body of the patient, so as to enable a correct transmission of the percussions (for example, hammer blows) to the rasp 50.

In fact, the handle 1 preferably comprises an abutment head 3 arranged at the first portion 11 and configured to be struck by a percussion element, for example a hammer, for which the inclination of the proximal portion 10 of the handle 1 in relation to the femur F is particularly ergonomic for the surgeon and enables the efficacious advancement of the rasp 50 in the femur F following a blow beaten on the abutment head 3.

The fact that the first axis A1 and the second axis A2 and/or the third axis A3 are transverse makes it possible, advantageously, to create a handle 1 wherein there are two different inclinations for the distal part 20 and for the proximal part 10. The fact that the two convexities are opposite to each other makes it possible, therefore, to create a handle 1 that is practical and ergonomic to use.

With reference to the first embodiment of the handle 1, illustrated in FIGS. 1A, 1B, and 2, the second axis A2 and the third axis A3 preferably coincide, so that the distal part 20 extends between the third portion 21 of the handle 1 and the sixth portion of the handle 24 along a single, main extension direction that coincides with the axes A2, A3.

In accordance with the first embodiment, the first angle α and the second angle β preferably have respective convexities turned towards opposite half-planes defined by the second axis A2 and by the third axis A3.

In particular, as illustrated in FIGS. 1A and 1B, the axes A1, A2, A3, and N lie on the same placement plane, still more preferably, a symmetry plane of the handle 1, so that the two convexities defined by the first angle α and by the second angle β lie on (i.e. are turned towards) opposite half-planes defined by the axes A2, A3.

With reference to the group of three k1, k2, k3 indicated in FIGS. 1A and 1B, therefore:
the axes A1, A2, A3, N lie within the plane passing through k1, k2, so that, as can be seen in FIG. 1B, the distal part 20 does not have a main extension component along k3; therefore, the offset of the handle 1 is nothing compared to the plane passing through k1, k2, the distal part 20 extends within the plane passing through k1, k2 in the direction +k1, +k2.

In accordance with a second embodiment of the handle 1 illustrated in FIGS. 4A, 4B, and 4C, on the other hand, the distal part 20 comprises a skew portion 25 extending, between the fourth portion 22 and the fifth portion 23 of the handle 1, along a skew axis S that is transverse in relation to the second axis A2 and to the third axis A3.

Thus, the fourth portion 22 is connected to the fifth portion 23 by means of the skew portion 25.

In other words, with reference to the FIG. 4A, a first plane P1 passing through the first axis A1 and the second axis A2 is offset, preferably parallel, in relation to a second plane P2 passing through the third axis A3 and through the normal axis N; in other words, between the first plane P1 and the second plane P2, there is an offset along the direction k3.

With reference to the group of three k1, k2, k3 indicated in FIGS. 4A, 4B, and 4C, therefore:
only the axes A1 and A2 lie within the plane P1 passing through k1, k2, so that the distal part 20 only extends in part within the plane passing through k1, k2 in the direction +k1, +k2,
the skew portion 25 extends in the direction +k1, +k2, +k3, defining an offset along k3 of the handle 1 in relation to the plane passing through k1, k2. Preferably, in addition, the first angle α and the second angle β have respective convexities turned in opposite directions in relation to the handle itself, and in particular in relation to a plane on which the second axis A2, the third axis A3, and the skew axis S lie.

Advantageously, the insertion of the rasp 50 in the medullary canal of the femur F, using a handle 1 with a skew portion 25 of the type shown in FIGS. 4A and 4B makes it possible to reduce the extra-rotation of the femur F that is necessary before inserting the rasp 50. In fact, the skew nature makes it possible to reach the access zone for accessing the femoral canal more easily, without the distal portion 20 interfering with the acetabular zone of the patient.

In particularly osteoporotic patients, the risk of femur F fractures is very high if the patient's leg undergoes a strong extra-rotation.

Typically, the surgeon, in fact, grasps the foot of the patient and rotates it, towards the floor, to obtain the rotation of the femur F that is necessary to expose the access zone for accessing the femoral canal in order to insert the rasp 50.

The femur F, in any case, does not precisely follow the foot's rotation due to kinematic loss at the knee joint, so that, to obtain, for example, a 90° rotation at the level of the greater trochanter of the femur F, the foot of the patient must be rotated by a rotation angle significantly greater than 90°. Osteoporotic patients often cannot bear this rotation, in any case, so that the rotation that can be obtained is less than necessary, when the operation is performed with a handle for a rasp without the skew portion. As a result, the access zone for the femoral canal will be less exposed to the surgeon and difficult to reach with the rasp 50. Thanks to the handle 1 with the skew portion 25, to which this invention relates, it is, in contrast, possible to reach the access zone for the femoral canal in a practical and efficacious manner, since the presence of the skew portion 25 makes it possible to partially deviate the extension of the distal portion 20 so that it does not interfere with the patient's anatomy, in particular with the pelvic bone.

With reference to the attached figures, the sixth portion 24 preferably extends along the normal axis N defining an extension portion 26 of the distal part 20: the connection surface 2, in this case, is thus arranged at the free end of the extension portion 26.

As can be seen in FIG. 2, the connection surface 2 preferably has, in addition, at least one mutual coupling element 4 configured to couple with the rasp 50, wherein, still more preferably, the mutual coupling element 4 is a pin extending along a prevailing extension direction that is parallel to the normal axis N.

In particular, the pin 4 is suitable for insertion into a coupling seat 51 of the rasp 50.

With reference to FIG. 2, and according to this invention, the handle 1 preferably comprises:
a joining element 5 configured to couple and uncouple to the rasp 50, and
a lever mechanism 6, connected to the joining element 5, arranged inside a cavity 7 of the handle 1 and configured to move the joining element 5 through the connection surface 2 along a coupling direction that is parallel to the normal axis N between a coupling position and an uncoupling position.

In other words, the surgeon, by activating the lever mechanism 6, can move the joining element 5, for example a pin, away from the connection surface 2, so that this is inserted inside a coupling seat 52 of the rasp 50, which is suitable for receiving it and holding it inside in the coupling position.

The surgeon, to uncouple the rasp 50, for example to replace it with a larger size, by activating the lever mechanism 6 can remove and disengage the joining element 5 from the coupling seat 52, by withdrawing it through the connection surface 2.

With reference to the attached figures, the handle 1 preferably comprises, in addition, a gripping and/or abutment element 8 arranged so that it straddles the second portion 12 and the third portion 21 and configured to be grasped by a user and/or to be struck by a percussion element, which is not illustrated.

The gripping and/or abutment element 8 preferably has the shape of a projecting wedge.

The gripping and/or abutment element 8 advantageously enables the surgeon, during use of the handle 1 connected to the rasp 50, to comfortably grasp the handle 1 for inserting and removing the rasp 50 in the/from the femoral canal C and to hit the handle 1 with a hammer to facilitate the extraction of the rasp from the canal C when fitted.

With reference to FIG. 2, according to an additional aspect of this invention, a kit is also provided for preparing a femoral canal comprising:
a handle 1 to which this invention relates, and
at least one rasp 50 extending along a prevailing extension axis X coinciding with an insertion axis Y of the rasp 50 inside the femur F for the preparation of a femoral canal C, wherein the rasp 50 being reversibly connectable to the handle 1 at the connection surface 2 along the connection axis Z.

In particular, the kit preferably comprises a plurality of rasps 50 of different sizes, so as to be able to rasp the femoral canal in order to prepare the femoral canal C adapting it to receive the stem of the prosthesis with dimensions suitable for the dimensions of the patient's femur F.

Also part of this invention is a device 100 comprising:
a handle 1 according to this invention, and
a rasp 50, preferably of the type described above;
wherein a convex inclination angle of the rasp γ is defined between the prevailing extension axis X of the rasp 50 and the third axis A3 of the handle.

In other words, the convex inclination angle of the rasp γ defines the angle between the prevailing extension direction of the end zone of the distal portion 20 (that which extends between the fifth portion 23 and the sixth portion 24) and the prevailing extension direction of the rasp 50.

In particular, for the first embodiment of the device 100, illustrated in FIGS. 1A-3, the convex inclination angle of the rasp γ defines the angle between the prevailing extension direction of the distal portion 20, i.e. the axes A2, A3, and the prevailing extension direction X of the rasp 50.

In particular, the inclination angle of the rasp γ and the second angle β both pass over the distal portion 20.

In addition, the first angle α and the inclination angle of the rasp γ preferably have respective convexities turned in opposite directions in relation to the handle 1 itself, or in relation to the distal portion 20 of the handle.

Advantageously, the double convexity makes it possible to create a device 100 that can be easily and efficiently inserted into the femur F without interfering with the patient's abdomen.

The inclination angle of the rasp γ preferably has a value ranging between 90° and 135°, still more preferably equal to 105°.

In accordance with the first embodiment, the first axis A1, the second axis A2, the third axis A3, the normal axis N, and the prevailing extension axis of the rasp X preferably lie on the same placement plane of the device 100.

A convex inclination angle of the proximal part δ part, with a value ranging between 0° and 45°, still more preferably equal to 30°, is preferably defined between the prevailing extension axis X of the rasp and the first axis A1 of the handle 1.

Advantageously, the value of the inclination angle of the proximal part δ (FIG. 1A) makes it possible to guarantee suitable ergonomics when the surgeon uses the device 100.

The abutment head 3 preferably has an essentially planar abutment surface 3a, so that a convex abutment angle ε (FIG. 1A) is defined between the normal of the abutment surface 3a and the prevailing extension axis X, the angle having a value ranging between 0° and 50°, preferably equal to 45°.

The normal axis N and the normal to the abutment surface 3a are preferably parallel.

The abutment surface 3a is preferably slightly spherical (i.e. it has a curvature radius tending to infinity) so that the surgeon is more likely to strike the central part of the spherical cap when inserting the rasp 50, to transmit an optimal percussion to the rasp, without dispersing the force.

Advantageously, the value of the abutment angle ε makes it possible to ensure that the thrusts imparted on the handle 1 are suitably transmitted to the rasp 50.

The surgical device 100 is, preferably, a stiff system, so that the proximal part 10, the distal part 20, and the rasp 50 cannot be moved in relation to each other and the angles described above cannot be altered.

With reference to the attached figures, the distal part 20 of the handle 1 and the proximal part 10 of the handle 1 are preferably joined to each other, and the distal part 20 is joined to the rasp 50, so that the surgical device 100 has a double curvature.

Also part of this invention is a device 100, not illustrated in the attached figures, in which the handle 1 and the rasp 50 are made of a single piece.

The operating method for preparing a femoral canal using the handle 1 and/or the device 100 and/or the kit to which this invention relates and in accordance with the two embodiments described involves, thus, the following steps:
cutting the leg of the patient at the front and separating the soft tissues so as to render the acetabular zone and that of the femoral head visible;
severing the femoral neck and removing the femoral head from the patient's body;
milling the acetabular cup to prepare it for an acetabular prosthetic cup;
positioning the prosthetic acetabular cup;
hyperextending the patient's leg and rotating the patient's leg externally;
inserting the rasp 50 and proceeding with rasping the femoral medullary canal until the desired size is obtained for inserting the definitive prosthetic stem;
inserting the definitive prosthetic stem Finally, the prosthetic head is inserted onto the definitive stem and the head is engaged inside the acetabular cup, rotating the leg again to return it to its natural position.

These steps do not involve femoral release, i.e. removing the femur from its natural seat and moving the upper part of the femur towards the wound. This invention achieves the proposed purposes, overcoming the drawbacks complained of in the prior art, and providing a versatile handle 1 for a rasp 50 that can be appropriately designed to adapt to the physiological needs of the patient. The invention also provides a surgical device 100 for preparing a femoral canal C, which reduces invasiveness and operating times by avoiding bone dislocation and trauma to the patient.

In particular, the device 100 makes it possible to avoid extracting the access area to the femoral canal, operating in greater safety.

The invention claimed is:

1. A surgical device comprising a broach handle and a rasp, the broach handle comprising:
a proximal part extending along a first axis between a first portion of the broach handle and a second portion of the broach handle; and
a distal part extending partially along a second axis between a third portion of the broach handle, connected to the second portion, and a fourth portion of the broach handle, and partially along a third axis between a fifth portion of the broach handle, connected to the fourth portion, and a sixth portion of the broach handle connectable to the rasp,
wherein the sixth portion of the broach handle has a connection surface for connecting to the rasp, the connection surface having a normal axis that defines a connection axis between the broach handle and the rasp,
wherein a first angle is defined between the first axis and the second axis, and a second angle is defined between the third axis and the normal axis,
wherein a first convex surface is defined between the first axis and the second axis, and a second convex surface is defined between the third axis and the normal axis,
wherein said first axis, said second axis, said third axis, and said normal axis lie on the same placement plane, and wherein an inclination angle of the proximal part is defined between a prevailing extension axis of the rasp and the first axis of the broach handle, the inclination angle of the proximal part ranging between 0° and 45°, wherein the prevailing extension axis of the rasp extends centrally through a length of the rasp.

2. The surgical device according to claim 1, wherein respective convexities of the first convex surface and the second convex surface are turned in opposite directions.

3. The surgical device according to claim 1, wherein the second axis and the third axis coincide.

4. The surgical device according to claim 3, wherein respective convexities of the first convex surface and the second convex surface are turned in opposite directions in relation to a transverse plane where the second axis and the third axis lie.

5. A surgical device comprising a broach handle and a rasp, the broach handle comprising:
a proximal part extending along a first axis between a first portion of the broach handle and a second portion of the broach handle; and
a distal part extending partially along a second axis between a third portion of the broach handle, connected to the second portion, and a fourth portion of the broach handle, and partially along a third axis between a fifth portion of the broach handle, connected to the fourth portion, and a sixth portion of the broach handle connectable to the rasp,
wherein the sixth portion of the broach handle has a connection surface for connecting to the rasp, the connection surface having a normal axis that defines a connection axis between the broach handle and the rasp,
wherein a first angle is defined between the first axis and the second axis, and a second angle is defined between the third axis and the normal axis,
wherein a first convex surface is defined between the first axis and second axis, and a second convex surface turned in a direction opposite the first convex surface is defined between the third axis and the normal axis,
wherein the distal part comprises a skew portion extending between the fourth portion and the fifth portion of the broach handle, along a skew axis that is transverse in relation to the second axis and the third axis, and
wherein an inclination angle of the proximal part is defined between a prevailing extension axis of the rasp and the first axis of the broach handle, the inclination angle of the proximal part ranging between 0° and 45°,
wherein the prevailing extension axis of the rasp extends centrally through a length of the rasp.

6. The surgical device according to claim 5, wherein respective convexities of the first convex surface and the second convex surface are turned in opposite directions in relation to a transverse plane where the second axis and the third axis lie.

7. The surgical device according to claim 5, wherein the first angle has a value ranging between 90° and 180°.

8. The surgical device according to claim 5, wherein the second angle has a value ranging between 125° and 165°.

9. The surgical device according to claim 5, wherein the sixth portion extends along the normal axis defining an extension portion of the distal part.

10. The surgical device according to claim 5, wherein the connection surface has at least one mutual coupling element configured to couple with the rasp, wherein said at least one mutual coupling element is a pin extending along an extension direction that is parallel to the normal axis.

11. The surgical device according to claim 5, the broach handle further comprising:
a joining element configured for being reversibly coupled to said rasp; and
a lever mechanism, connected to the joining element, arranged inside a cavity of the broach handle and configured to move the joining element through the connection surface along a coupling direction that is parallel to the normal axis between a coupling position and an uncoupling position.

12. The surgical device according to claim 5, the broach handle further comprising an abutment head arranged at the first portion and configured to be struck by a percussion element.

13. The surgical device according to claim 5, the broach handle further comprising a gripping and/or abutment element arranged so that it straddles the second portion and the third portion and configured to be grasped by a user and/or to be struck by a percussion element.

14. The surgical device according to claim 1, wherein
the rasp is configured to be inserted into a femur and extends along the prevailing extension axis of the rasp for preparation of a femoral canal, said rasp being connected to the broach handle at the connection surface along the connection axis,
wherein an inclination angle of the rasp is defined between the prevailing extension axis of the rasp and the third axis of the broach handle.

15. The surgical device according to claim 14,
wherein respective convexities of the first convex surface and the inclination surface of the rasp are turned in opposite directions.

16. The surgical device according to claim 15, wherein the inclination angle of the rasp has a value ranging between 90° and 135°.

17. The surgical device according to claim 15, wherein the first axis, the second axis, the third axis, the normal axis, and the prevailing extension axis of the rasp lie within the same placement plane of the device.

18. The surgical device according to claim 14, wherein the broach handle comprises an abutment head arranged at the first portion of the broach handle and configured to be struck by a percussion element, wherein said abutment head has a planar abutment surface, so that an abutment angle is defined between a normal axis of said abutment surface and the prevailing extension axis of the rasp, the abutment angle having a value ranging between 0° and 50°.

19. The surgical device according to claim 14, wherein the distal part of the broach handle and the proximal part of the broach handle are joined to each other and wherein the distal part of the broach handle is joined to the rasp, so that the surgical device has a double curvature.

20. A surgical device for preparation of a femoral canal comprising a broach handle and a rasp irreversibly connected to each other,
wherein said rasp is configured to be inserted into a femur and extends along a prevailing extension axis of the rasp for the preparation of a femoral canal,
wherein said broach handle comprises:
a proximal part extending along a first axis between a first portion of the broach handle and a second portion of the broach handle; and
a distal part extending partially along a second axis between a third portion of the broach handle connected to the second portion, and a fourth portion of the broach handle, and partially along a third axis between a fifth portion of the broach handle connected to the fourth portion and a sixth portion of the broach handle connectable to the rasp, wherein a first convex surface is defined between the first axis and the second axis and an inclination angle of the rasp is defined between the prevailing extension axis of the rasp and the third axis of the broach handle, and wherein said first axis, said second axis, said third axis, and said prevailing extension axis of the rasp lie on the same placement plane.

21. A surgical device for preparation of a femoral canal comprising a broach handle and a rasp irreversibly connected to each other, wherein said rasp is configured to be inserted into a femur and extends along a prevailing extension axis of the rasp for the preparation of a femoral canal, and wherein said broach handle comprises:

a proximal part extending along a first axis between a first portion of the broach handle and a second portion of the broach handle; and a distal part extending partially along a second axis between a third portion of the broach handle, connected to the second portion, and a fourth portion of the broach handle, and partially along a third axis between a fifth portion of the broach handle, connected to the fourth portion, and a sixth portion of the broach handle connected to the rasp, wherein a first convex surface is defined between the first axis and the second axis and an inclination angle of the rasp is defined between the prevailing extension axis of the rasp and the third axis of the broach handle, and wherein the distal part of the broach handle comprises a skew portion extending between the fourth portion and the fifth portion of the broach handle, along a skew axis that is transverse in relation to the second axis and the third axis.

22. A broach handle for a rasp comprising:

a proximal part extending along a first axis between a first portion of the broach handle and a second portion of the broach handle; and a distal part extending partially along a second axis between a third portion of the broach handle, connected to the second portion, and a fourth portion of the broach handle, and partially along a third axis between a fifth portion of the broach handle, connected to the fourth portion, and a sixth portion of the broach handle connectable to a rasp, wherein the sixth portion of the broach handle has a connection surface for connecting to the rasp, the connection surface having a normal axis that defines a connection axis between the broach handle and the rasp, wherein the broach handle comprises an abutment head arranged at the first portion of the broach handle, the abutment head having a planar abutment surface configured to be struck by a percussion element, wherein an axis normal to the abutment surface is parallel to the normal axis of the connection surface, wherein a first angle is defined between the first axis and the second axis, and a second angle is defined between the third axis and the normal axis, wherein a first convex surface is defined between the first axis and the second axis, and a second convex surface is defined between the third axis and the normal axis, and wherein said first axis, said second axis, said third axis, and said normal axis lie on the same placement plane.

23. A broach handle for a rasp comprising:

a proximal part extending along a first axis between a first portion of the broach handle and a second portion of the broach handle; and a distal part extending partially along a second axis between a third portion of the broach handle, connected to the second portion, and a fourth portion of the broach handle, and partially along a third axis between a fifth portion of the broach handle, connected to the fourth portion, and a sixth portion of the broach handle connectable to a rasp, wherein the sixth portion of the broach handle has a connection surface for connecting to the rasp, the connection surface having a normal axis that defines a connection axis between the broach handle and the rasp, wherein the broach handle comprises an abutment head arranged at the first portion of the broach handle, the abutment head having a planar abutment surface configured to be struck by a percussion element, wherein an axis normal to the abutment surface is parallel to the normal axis of the connection surface, wherein a first angle is defined between the first axis and the second axis, and a second angle is defined between the third axis and the normal axis, wherein a first convex surface is defined between the first axis and the second axis, and a second convex surface is defined between the third axis and the normal axis, and wherein the distal part comprises a skew portion extending between the fourth portion and the fifth portion of the broach handle, along a skew axis that is transverse in relation to the second axis and the third axis.

* * * * *